United States Patent [19]

Noppel et al.

[11] Patent Number: 5,069,208
[45] Date of Patent: Dec. 3, 1991

[54] THERAPEUTIC DEVICE COMPRISING A MASS OF A THERMALLY ACTIVE MATERIAL

[75] Inventors: René Noppel, Préverenges; Kurt Wuillemin, Fribourg, both of Switzerland

[73] Assignee: Term-ac S.A., Fribourg, Switzerland

[21] Appl. No.: 455,924

[22] Filed: Dec. 26, 1989

Related U.S. Application Data

[63] Continuation of Ser. No. 180,113, filed as PCT/CH87/00029 Mar. 9, 1987, published as WO87/06825 Nov. 11, 1987, abandoned.

[30] Foreign Application Priority Data

May 16, 1986 [CH] Switzerland .................. 2000/86

[51] Int. Cl.5 .............................................. A61F 7/02
[52] U.S. Cl. ................................. 128/403; 128/402; 383/901; 62/530
[58] Field of Search ............... 128/399, 402, 403, 379, 128/380; 62/530; 383/901

[56] References Cited

U.S. PATENT DOCUMENTS

| 2,547,886 | 4/1951 | Poux | 62/530 |
| --- | --- | --- | --- |
| 2,595,328 | 5/1952 | Bowen | 128/403 |
| 2,715,315 | 8/1955 | Giardini | 62/530 |
| 3,258,065 | 6/1966 | Ward | 62/530 |
| 3,913,559 | 10/1975 | Dandliker | 128/403 |
| 4,527,566 | 7/1985 | Abare | 128/402 |
| 4,592,358 | 6/1986 | Westplate | 128/902 |
| 4,596,250 | 6/1986 | Beisang, III et al. | 128/403 |
| 4,676,247 | 6/1987 | Van Cleve | 128/403 |

FOREIGN PATENT DOCUMENTS

| 3141191 | 3/1985 | Fed. Rep. of Germany . | |
| --- | --- | --- | --- |
| 1365666 | 7/1963 | France . | |
| 172581 | 9/1984 | Japan | 62/530 |
| 8603400 | 6/1986 | PCT Int'l Appl. . | |
| 605400 | 9/1978 | Switzerland | 128/402 |
| 952455 | 3/1964 | United Kingdom | 62/530 |
| 2160965 | 1/1986 | United Kingdom . | |

Primary Examiner—Edward M. Coven
Assistant Examiner—Mark S. Graham
Attorney, Agent, or Firm—Oliff & Berridge

[57] ABSTRACT

A pad for hot or cold therapeutic applications comprises a fluid-tight and flexible covering (13) which may be of a double or triple composite sheet, containing a sheet of polyethylene. Enclosed in the covering are, on the one hand, a mass of heat-exchanging fluid (12) which may be a gel, an emulsion, or another stable fluid, having a high specific heat, and, on the other hand, a set of cells (10). Each cell comprises, in a likewise fluid-tight and flexible covering (14), a mass of thermally active material (11) which presents a change of state with latent heat of transformation as high as possible, in a range of temperature adapted to the application aimed at. For a cold application, the temperature of transformation of the material will have a value between −15° C. and +15°C., for example. For a hot application, the temperature will be between +35° C. and +70° C., for example.

14 Claims, 2 Drawing Sheets

THERAPEUTIC DEVICE COMPRISING A MASS OF A THERMALLY ACTIVE MATERIAL

This is a continuation of application Ser. No. 07/180,113 filed PCT/CH87/00029 Mar. 9, 1987, published as WO87, now abandoned.

BACKGROUND OF THE INVENTION

It is known that certain therapeutic treatments comprise the application of cold masses or of hot masses to the parts of the body to be treated. As an example of cold therapy, the treatment of contusions or of operative incisions may be cited. Used for that purpose are cold pads which warm up gradually starting from a temperature of about 0° C. up to body temperature. The materials used, e.g., mixtures of water and glycol, release the kilocalories which they have stored according to a constant-elevation process, thus in a linear manner. In order for their cooling effect to last long enough, it is therefore necessary that they be highly cooled. However, the application of very low-temperature bodies to the skin may be disagreeable and even bring about local frostbite. Added to this is that the efficiency of the application of these methods from the point of view of the desired therapeutic effect is far from being optimal.

Thus, most of the known cooling pads currently on the market have drawbacks. As indicated above, they rapidly lose their effect, so that they must be changed frequently, which brings about temperature variations unfavorable for the therapy aimed at and requires a considerable commitment from the nursing personnel. Certain known cooling pads, such as that described in German patent DE 31 41 191, for example, have the drawback that the thermally active material does not occupy the whole of the volume of the pad since it forms an emulsion with a non-active emulsifier, which reduces its effectiveness.

In order partially to remedy these drawbacks, and especially the rapid variation of the temperature of the cold pads upon contact with the body, it has already been contemplated to use ice cubes, which have the advantage of remaining at the temperature of 0° C. as long as they have not entirely melted. The ice can indeed absorb from the body with which it is in contact an amount of heat equal to its latent heat of fusion, which is 314 KJ/kg. In melting, however, the blocks of ice wet the articles of clothing with which they are in contact, and moreover, in the solid state, they generally have sharp edges which can injure the skin.

Likewise known, in particular from U.S. Pat. No. 4,527,566, are flexible bandages equipped with pockets capable of receiving blocks of ice or hot cells, but this bandage remedies the above-mentioned drawbacks only partially.

The French patent FR 1,365,666 also contains a description of a packaging for masses of a freezable liquid. These masses are enclosed in recipients which are themselves placed in packages of diverse shapes and constructions.

SUMMARY OF THE INVENTION

The object of the present invention is to create a simple therapeutic device, capable of being used under conditions very different from one another, handy to use, and answering better than the devices known until now the practical and therapeutic requirements to which devices of this type are subjected.

To this end, the main subject of the present invention is a cell for a thermal-action therapeutic device, characterized in that it is made up of a mass of a thermally active material which presents a change of state at a predetermined temperature, and of a fluid-tight closed covering with thin walls enclosing the said mass of thermally active material.

In a first particular aspect, the invention relates to a thermal-action therapeutic device, comprising a bandage with a plurality of pockets, characterized in that the pockets are arranged for receiving cells such as defined above, their number, their shape, and their dimensions being determined as a function of the characteristics of the cells so as to permit the obtaining of a hot or cold therapeutic effect according to the cells used.

A further subject of the invention is a thermal-action therapeutic device comprising a wrapping containing a heat-exchanging agent, characterized in that a plurality of cells are embedded in the said heat-exchanging agent.

BRIEF DESCRIPTION OF THE DRAWINGS

Various embodiments of the subject of the invention will be described below by way of example, referring to the appended drawing, of which.

DETAILED DESCRIPTION OF THE INVENTION

Figure 1:
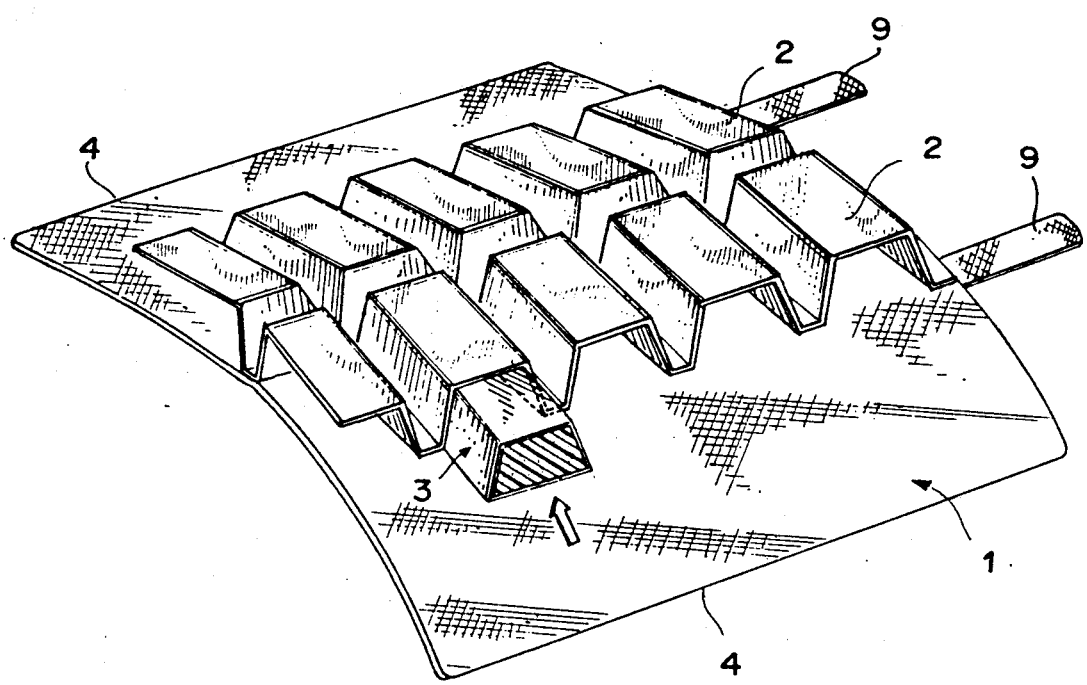
FIG. 1 is a partially cut-away perspective view of the first embodiment.

As is seen in the drawing, the device is composed essentially of a bandage 1 provided with a certain number of pockets 2, all having the same dimensions, and of a set of cells 3 which contain the thermally active material.

The shape and the make-up of the bandage 1 may be very variable. According to FIG. 1, the bandage is made up of a basic segment of cloth 4 on which other elements of cloth delimiting the pockets 2 are fixed. These pockets are disposed in two rows. They have approximately the shape of rectangular parallelepipeds which are adapted to the dimensions of the cells 3, as will be seen below. The bandage may be entirely formed of cloth or of sheets of plastic material. In the embodiment depicted, the longitudinal edges of the base piece 4 may be folded over the two rows of pockets 2 in order to close the latter. Of course, straps (not shown) or any other element permitting the bandage to be fixed to the part of the body which must be treated, e.g., around a leg or around an arm, if desired, may be fixed to this base piece 4. However, it is well understood that this bandage may likewise be fixed, for example, by pieces of adhesive tape adhering directly to the body.

As is seen at the left-hand end of FIG. 1, the pockets 2 are open on one of their faces and closed on the other sides. Straps 9 permit the bandage to be fixed to the part of the body to be treated, e.g., around an arm or a leg.

Figure 2:
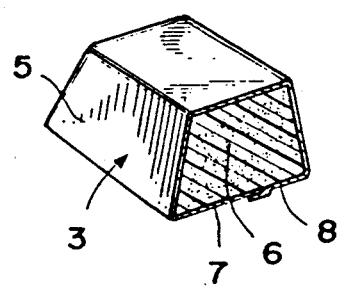
FIG. 2 is a perspective view, likewise cut away, showing a cell containing the thermally active material.

The cells 3 are each composed of a thin-walled covering 5 which will preferably be of a composite material containing a sheet of aluminum, or of an air- and moisture-tight plastic material, and a filling mass 6 which is made up of the thermally active material which it is desired to use. The volume of the cells may be standardized. For the embodiment described here, it will be, for example, from 5 to 30 cm$^3$. Of course, the volume and the shape of the cells correspond to the volume and the shape of the pockets 2. In FIGS. 1 and 2 trapezoid-shaped blocks are shown. The cells may be formed by shaping a plastic material and welding the lid on the part thus molded. The coverings 5 may likewise be stratified sheets which have been blanked, folded, and closed by welding. Thus, in FIG. 2, the lower walls of the cells are formed of two marginal portions 7 and 8 of a starting sheet, welded onto one another by overlapping.

The material 6 contained in the cells is a material which undergoes a phase change at a predetermined temperature. Preferably, this phase change will be a change from the liquid phase to the solid phase or vice versa. The transformation temperature may be fixed at a value between $-15°$ and $+15°$ C. for cold-therapy application. On the contrary, this transformation temperature may be fixed at a value between $+35°$ and $+70°$ C. for hot-therapy application. The thermally active material will be chosen in such a way that its latent heat fusion per unit of volume is as high as possible. Thus, for example, in the case of a cold-therapy application, the thermally active material may be a chemical compound of the group of hydrates of salts or, as the case may be, water. In the case of a hot-therapy application, other materials may be used, e.g., saturated or unsaturated hydrocarbon-base compounds, or also hydrates of salts.

The device described permits associating series of cells, such as the cells 3 of different materials having well-defined temperatures of transformation, with bandages of different shapes and of different dimensions capable of being applied to different parts of the human body. The assembly therefore yields great flexibility of use. The treatment presents an improved effectiveness relative to the use of materials which warm up gradually upon contact with the body since the bandage applied to the body is capable of absorbing a large amount of heat while remaining at a well-defined temperature level, easy for the patient to bear, but efficient as to the thermal effect aimed at. As the case may be, cells having two different transformation temperature may even be combined in the same bandage in order to obtain a treatment at two successive temperature levels.

Of course, for improving the ease of use, the different cells 3 can be marked in order to permit spotting of their temperature of transformation. They will be held ready for use, in appropriate cold chambers for the cold cells, in hot enclosures for the other cells intended for the applications at high temperature. The assembly of the elements described permits an efficient application of the therapeutic treatments by application of heat or cold, while limiting the commitment of the nursing personnel.

Figure 3:
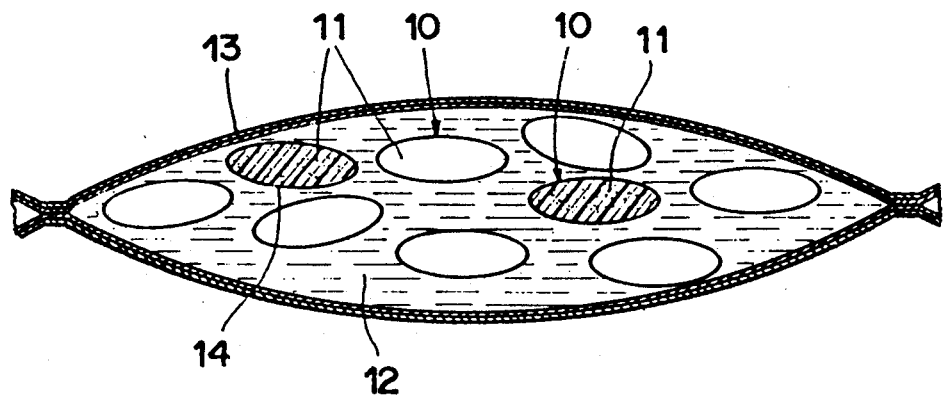
FIG. 3 is a sectional view of the second embodiment of the therapeutic device.

FIG. 3 illustrates another example of application of the principle set forth above: instead of using cells such as the cells 3 which are introduced into the pockets of a bandage 1, the cells are embedded in a mass of a soft heat-exchanging body, itself enclosed within a closed covering which is fluid-tight, flexible, and deformable.

Thus, FIG. 3 shows completely closed cells 10, each containing a predetermined mass of a thermally active material, the latter being designated by 11. The cells 10 are themselves embedded in a gel or an emulsion designated by 12, itself enclosed within a covering 13. In this case, the doses of thermo-active material contained in the cells will be smaller than in the case of the first application. Their volume will be, for example, from 0.05 to 1 cm$^3$. These doses of thermally active materials will be surrounded by a film of plastic material forming a fluid-tight closed covering with thin walls. For producing this covering, the same processes can be used as for the coverings of the cells 3 depicted in FIG. 2. The shape of the cells will preferably be different from those depicted in FIG. 2. For example, spherical cells may be provided for, on condition that the material of the covering is elastically extensible, in such a way that the variations in volume resulting from a change of phase may be absorbed. However, ellipsoid shapes may likewise be provided, for example, or in general shapes deviating from the sphere, so that the variations in volume due to the change of phases may be compensated for by a variation in shape. In one application, the cells may be formed by introducing the thermally active products into a continuous tube formed of the material of the covering. Next, the tube is pinched at intervals and welded to itself, then severed, which yields the thermally active cells. Besides the products mentioned above, studies have shown that other materials are likewise suitable, such as hydrated salts, certain eutectics, hydrocarbons, for example. Water has already been mentioned. When water or a saline solution is used, it will be advantageous to add additives capable of avoiding the formation of points of crystallization at the time of freezing, and the same for avoiding the phenomenon of supercooling at the time of cooling.

The mass in which the cells of FIG. 3 are embedded is a heat-exchanging fluid which will preferably present certain characteristics such as a high specific heat, good internal fluidity so that the shape of the outer wrapping may vary and adapt itself to the parts of the body to which the device is applied, and finally good chemical and physical stability. Certain known gels or emulsions answer the requirements particularly well. As the case may be, the emulsion may be constituted in such a way that the disperse phase itself presents a change of state in the course of the thermal evolution of the device. In this case, the temperature of transformation of this disperse phase will be close to the temperature of transformation of the thermally active material lodged in the cells. The evolution of the device will permit using the latent heat of transformation of the gel or the emulsion in which the globules are embedded.

Finally, the outer covering will preferably be a bag of flexible plastic material closed fluid-tightly, e.g., a polyethylene bag. The use of packaging such as described above permits an optimum contact to be obtained between the active material and the part of the human body to be treated. Generally, the use of wrappings according to FIG. 3 presents great advantages. The ease of use, of storage, of maintenance of the bags described, is very great. They may easily be washed. The material of the covering is very smooth and flexible, which facilitates the conformation of the bag to the part of the body to which it is applied. The conformation of the gel or the emulsion also facilitates this shaping. The bag may furthermore be colored or bear inscriptions. It may be provided with a film of a sensitive material capable of indicating whether the temperature of transformation has been reached.

Figure 4:
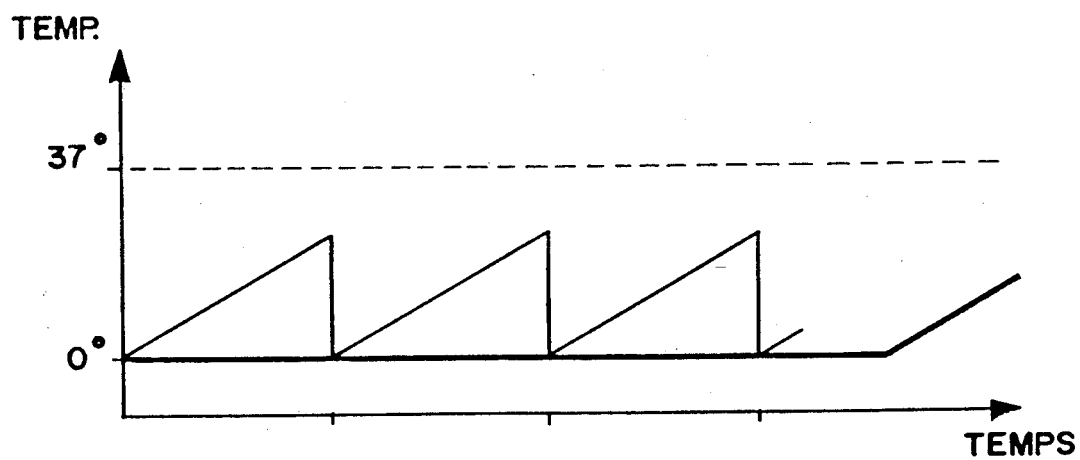
FIG. 4 is a graph showing the application of the device.

Finally, FIG. 4 shows the result of comparative tests which have been carried out. Whereas with an ordinary application, the temperature rises gradually as soon as the object is in contact with the body, so that it is necessary to change the application, e.g., every quarter of an hour, with the device according to the invention, the temperature of 0° C. is maintained for a duration which is a multiple of that recorded until now. A useful duration of use of one hour is easily reached if the cells are frozen at 0° C., for example. The mass of heat-exchanging fluid and the walls of the cells and of the bag form barriers which slightly raise the temperature upon contact with the body. Hence this temperature is on the order of a few degrees, and the application is felt as being decidedly more agreeable, while still keeping the long-lasting temperature level represented by the diagram.

What is claimed is:

1. A thermal-action therapeutic device comprising:
    a heat-exchanging agent comprising a non-gaseous fluid;
    a number of independent cells, each comprising a mass of thermally active material which undergoes a change of state at a predetermined temperature and a fluid-tight closed covering with thin walls enclosing each cell of said mass of thermally active material, said cells being embedded in and independently movable within said heat exchanging agent; and
    a closed fluid-tight wrapping wrapped around said heat exchanging agent and said independent cells.

2. A therapeutic device according to claim 1, wherein the heat-exchanging agent is a gel or an emulsion.

3. A therapeutic device according to claim 1, wherein the wrapping is a flexible, closed bag.

4. A device according to claim 1, wherein the wrapping comprises a sheet of polyethylene, of nylon, of PVC, or of polypropylene.

5. A device according to claim 1, wherein the wrapping is made up of a composite sheet having a constitution capable of guaranteeing the fluid-tightness and the flexibility of the device, the device being used as a hot or cold pad.

6. A device according claim 1, wherein the thermally active material is a material which undergoes a change of state from the solid phase to the liquid phase or vice versa, the temperature of transformation being between −15° C. and +15° C.

7. A device according to claim 1, wherein the covering comprises a sheet of aluminum.

8. A device according to claim 1, wherein the covering is formed of a stratified, air-tight and mositure-tight sheet of a plastic material.

9. A device according to claim 1, said cells being non-spherical so as to be able to absorb variations in volume by variations in shape.

10. A device according to claim 1, wherein the covering is conformed so as to permit a variation in volume at the time of the change of state of the thermally active material.

11. A device according to claim 10, wherein the material of the covering is capable of stretching.

12. A device according to claim 1, wherein the thermally active material is a salt, a hydrated salt, a eutectic, a hydrocarbon, or water.

13. A device according to claim 1, wherein the thermally active material is a material which undergoes a change of state from the solid phase to the liquid phase or vice versa, the temperature of transformation being between +35° and +70° C.

14. A device according to claim 1, wherein said heat-exchanging agent is in a form selected from the group of forms consisting of gel and emulsion.

* * * * *